United States Patent
Almulhim

(10) Patent No.: US 12,220,110 B1
(45) Date of Patent: Feb. 11, 2025

(54) SELF-FIXING TRANSPARENT PROCTOSCOPE

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/373,456

(22) Filed: Sep. 27, 2023

(51) Int. Cl.
| | |
|---|---|
| *A61B 1/31* | (2006.01) |
| *A61B 1/00* | (2006.01) |
| *A61B 1/06* | (2006.01) |
| *A61B 90/30* | (2016.01) |

(52) U.S. Cl.
CPC ............ *A61B 1/31* (2013.01); *A61B 1/00066* (2013.01); *A61B 1/00148* (2022.02); *A61B 1/0684* (2013.01); *A61B 2090/309* (2016.02)

(58) Field of Classification Search
CPC ....... A61B 1/31; A61B 17/02; A61B 17/0206; A61B 17/3423; A61B 2017/0212; A61B 2017/345–3452
See application file for complete search history.

(56) References Cited

U.S. PATENT DOCUMENTS

| | | | | |
|---|---|---|---|---|
| 4,621,619 | A * | 11/1986 | Sharpe | A61B 17/02 128/DIG. 15 |
| 2005/0277811 | A1* | 12/2005 | Richards | A61B 1/00105 600/184 |
| 2008/0275306 | A1* | 11/2008 | Rebuffat | A61B 1/32 600/184 |
| 2010/0280523 | A1* | 11/2010 | Chen | A61B 1/31 606/110 |

(Continued)

FOREIGN PATENT DOCUMENTS

| | | | | |
|---|---|---|---|---|
| GB | 2466985 | A * | 7/2010 | A61B 1/303 |

OTHER PUBLICATIONS

Smailmedical, "Proctoscope/anoscope with light", Youtube video, First available online Mar. 17, 2023.

(Continued)

*Primary Examiner* — Eduardo C Robert
*Assistant Examiner* — Michelle C Green
(74) *Attorney, Agent, or Firm* — Nath, Goldberg & Meyer; Joshua B. Goldberg

(57) ABSTRACT

A method for diagnosing and surgically removing gastrointestinal disorders in an anus and a rectum of a patient includes placing a first plurality of re-peelable double sided self-adhesive tapes around an anal area of the patient. Pressing an on/off button on a cordless LED light to turn the LED light on. Inserting a proctoscope into the anus of the patient. Aligning a plurality of handles of the proctoscope (Continued)

with the first plurality of re-peelable double sided self-adhesive tapes as the proctoscope is slowly pressed into the anus. Pushing the plurality of handles against a buttock area of the patient while maintaining the alignment between the plurality of handles and the first plurality of re-peelable double sided self-adhesive tapes thereby adhesively attaching the second plurality of re-peelable double sided self-adhesive tapes of the plurality of handles with the first plurality of re-peelable double sided self-adhesive tapes.

14 Claims, 4 Drawing Sheets

(56)  References Cited

U.S. PATENT DOCUMENTS

| | | | | |
|---|---|---|---|---|
| 2011/0087075 | A1* | 4/2011 | Wenchell | A61B 17/0218 600/235 |
| 2020/0360048 | A1 | 11/2020 | White et al. | |
| 2021/0153734 | A1* | 5/2021 | Stevenson | A61B 1/32 |

OTHER PUBLICATIONS

Hensley Medical Supplies, "Proctolux", Youtube video, First available online Jan. 5, 2015.

Your Friendly Proctologist, "What is a proctoscope or proctoscopy? How is it done and is it dangerous?", Youtube video, First available online Aug. 12, 2021.

Essam Ghareeb-Medical Dir., "Haemoband Protoscope, Sigmoidoscope and Combo Set", Youtube video, First available online Feb. 10, 2020.

Hospitalbuy, "Disposable Sapimed Proctoscope", online website, First available online Feb. 9, 2023.

Sapimed, "Disposable medical proctoscopes", brochure, First available online Aug. 17, 2016.

Smailmedical, "Anoscope", Youtube video, First available online Jun. 30, 2021.

Indru Khubchandani et al., "Surgical Treatment of Hemorrhoids", Springer Science & Business Media, pp. 25 and 78, 2008.

Doctor Vinnie "How Does an ANOSCOPE Work?", Youtube video, First available online Jan. 17, 2023.

* cited by examiner

SELF-FIXING TRANSPARENT PROCTOSCOPE

FIELD AND BACKGROUND

The disclosure of the present application relates to an anal and rectal surgical diagnostic kit, and particularly to a kit and a method for diagnosing and surgically removing gastrointestinal disorders in the anus and the rectum of a patient.

DESCRIPTION OF THE PRIOR ART

A proctoscope is a rigid, thin hollow tube instrument with a light source. A proctoscopy (also known as rigid sigmoidoscopy) is a procedure for examining an anus and a rectum of a patient using the proctoscope. A proctoscopy is conducted by a doctor to detect gastrointestinal disorders such as, but not limited to, abnormal growth of the tissues, hemorrhoids, rectal bleeding, rectal polyps, and rectal or colon cancer.

During a proctoscopy procedure, the patient may be required to lay on their side with their knees bent or rest on their knees under their chest. The doctor then performs a preliminary rectal exam with a gloved lubricated finger to check for sore spots or blockages. Afterward, the proctoscope is lubricated and inserted slowly into the anus and the rectum of the patient. During examination, the doctor may hold the proctoscope with one hand while inspecting the anus and the rectum via the proctoscope. If surgery is determined to be necessary during the examination, the doctor may need to insert multiple surgical tools inside the proctoscope to surgically remove the target tissue(s) such as hemorrhoid, polyp, and/or or cancer tissues. In such situation, it becomes challenging for the doctor to operate the multiple surgical tools while maintaining stability of the proctoscope.

Thus, an anal and rectal surgical diagnostic kit for solving the aforementioned problems is desired.

SUMMARY

The present subject matter relates to an anal and rectal surgical diagnostic kit which, in one non-limiting embodiment, comprises a first plurality of re-peelable double sided self-adhesive tapes configured to be placed around an anal area of a patient; and a proctoscope comprising: a longitudinal body having a first portion, a second portion, and a third portion, the second portion being located between the first portion and the third portion, the third portion being a converging portion having a closed end and the first portion being a non-converging portion having an open end, each of the first portion, the second portion, and the third portion of the proctoscope having a top surface, a plurality of middle surfaces, and a bottom surface, wherein the top surfaces and the plurality of middle surfaces of each of the first portion, the second portion, and the third portion are solid and the bottom surfaces of at least the first portion and the second portion are hollow; a plurality of handles attached to the longitudinal body, wherein each of the plurality of handles are attached at an outer region of each of the plurality of middle surfaces of the first portion of the proctoscope; a second plurality of re-peelable double sided self-adhesive tapes attached to the plurality of handles configured to adhesively attach to the first plurality of re-peelable double sided self-adhesive tapes, wherein each of the second plurality of re-peelable double sided self-adhesive tapes are attached to a side of each of the plurality of handles facing in a direction toward the converging portion of the third portion of the proctoscope; and a cordless LED light attached to an inner region of the top surface of the first portion of the proctoscope configured to light an internal area of the anus and the rectum of the patient, wherein the cordless LED light comprises an on/off button.

In an embodiment, the first plurality of re-peelable double sided self-adhesive tapes comprises four re-peelable double sided self-adhesive tapes.

In an embodiment, the longitudinal body is U-shaped.

In another embodiment, the longitudinal body and the plurality of handles are transparent.

In another embodiment, the plurality of handles comprises two handles.

In a further embodiment, each of the plurality of handles comprises an angular surface.

In an embodiment, the second plurality of re-peelable double sided self-adhesive tapes comprises two re-peelable double sided self-adhesive tapes.

In a further embodiment, the present subject matter relates to a method of using the anal and rectal surgical diagnostic kit described above for diagnosing and surgically removing gastrointestinal disorders in the anus and the rectum of the patient, the method comprising: placing the first plurality of re-peelable double sided self-adhesive tapes around the anal area of the patient; pressing the on/off button on the cordless LED light to turn the LED light on; inserting the converging portion of the third portion of the proctoscope into the anus of the patient; aligning the plurality of handles with the first plurality of re-peelable double sided self-adhesive tapes as the proctoscope is slowly pressed into the anus; and pushing the plurality of handles against a buttock area of the patient while maintaining the alignment between the plurality of handles and the first plurality of re-peelable double sided self-adhesive tapes thereby adhesively attaching the second plurality of re-peelable double sided self-adhesive tapes with the first plurality of re-peelable double sided self-adhesive tapes.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
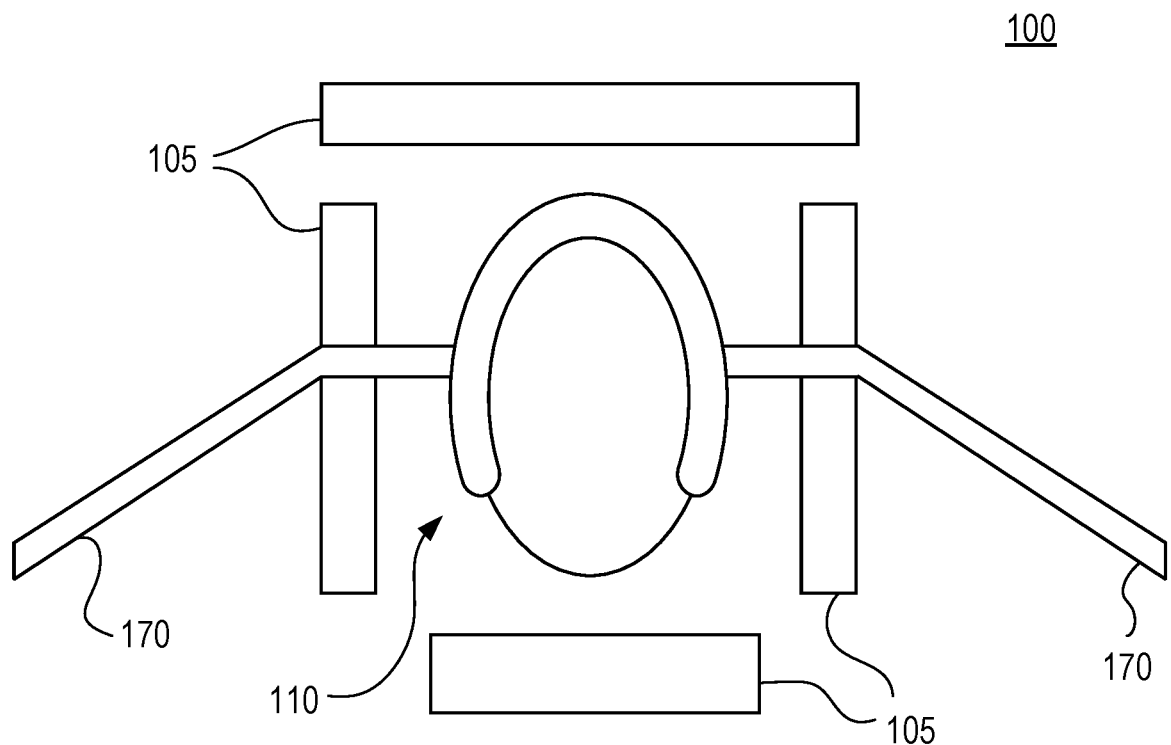
FIG. 1 depicts an anal and rectal surgical diagnostic kit which includes a first plurality of re-peelable double sided self-adhesive tapes placed around an anal area of a patient and a proctoscope inserted into an anus of the patient.

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Figure 2A:
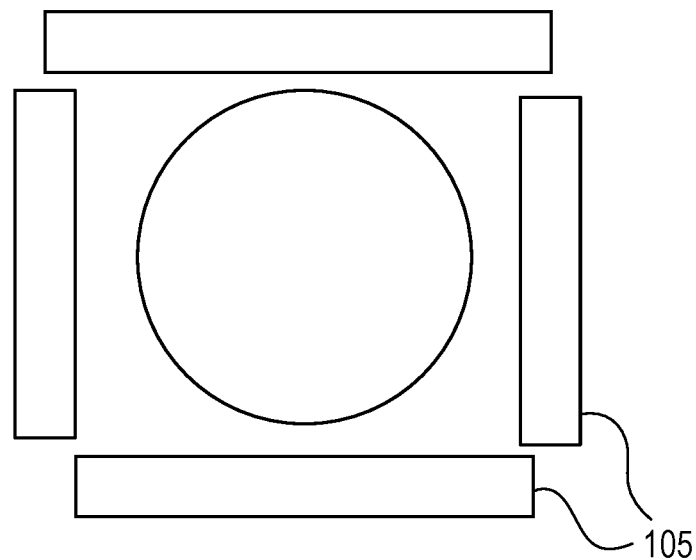
FIGS. 2A-2B depict the first plurality of re-peelable double sided self-adhesive tapes placed around the anal area of the patient without the proctoscope (FIG. 3A) with each of the first plurality of re-peelable double-sided self-adhesive tape having a defined dimension (FIG. 3B).
Figure 2B:
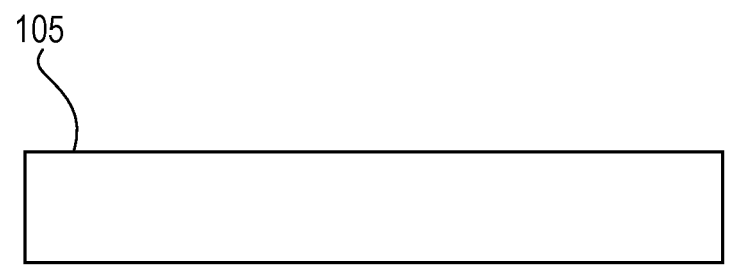
Figure 3:
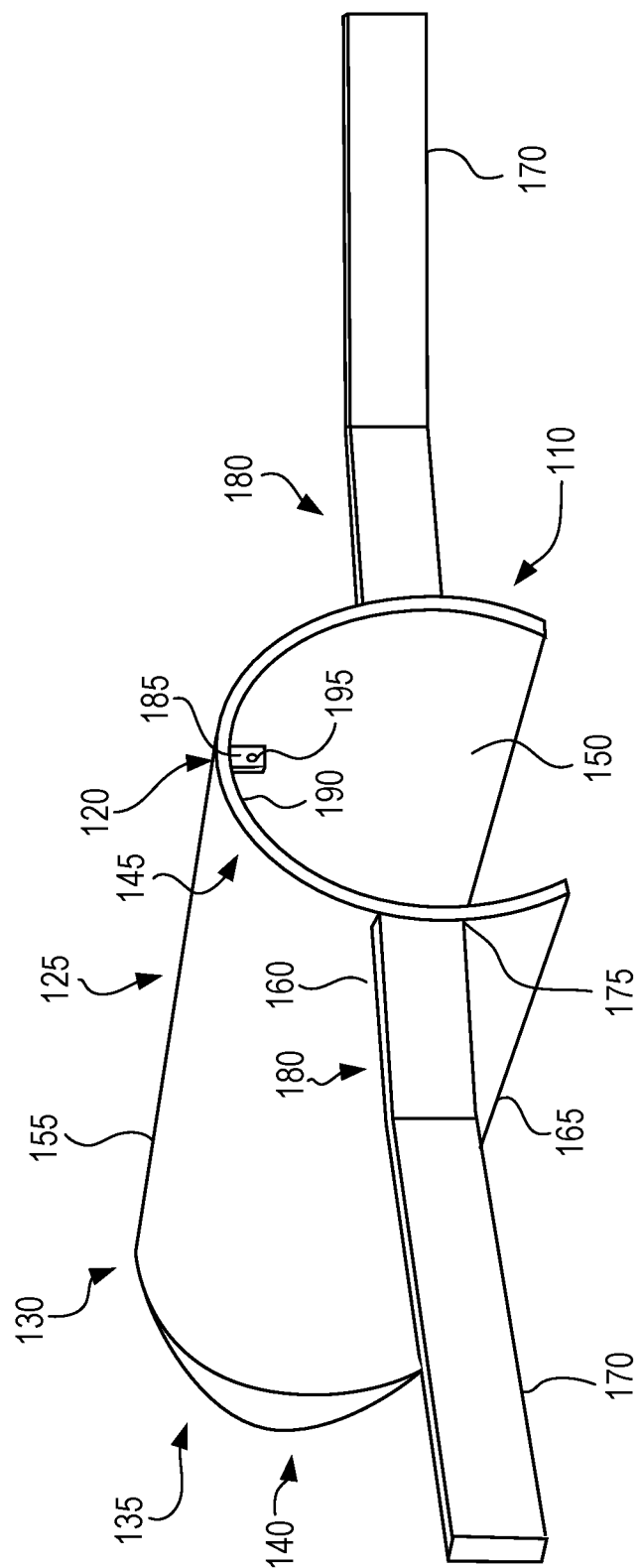
FIG. 3 depicts a side view of the proctoscope with the LED light and the second plurality of re-peelable double-sided self-adhesive tape on each handle of the proctoscope.
Figure 4:
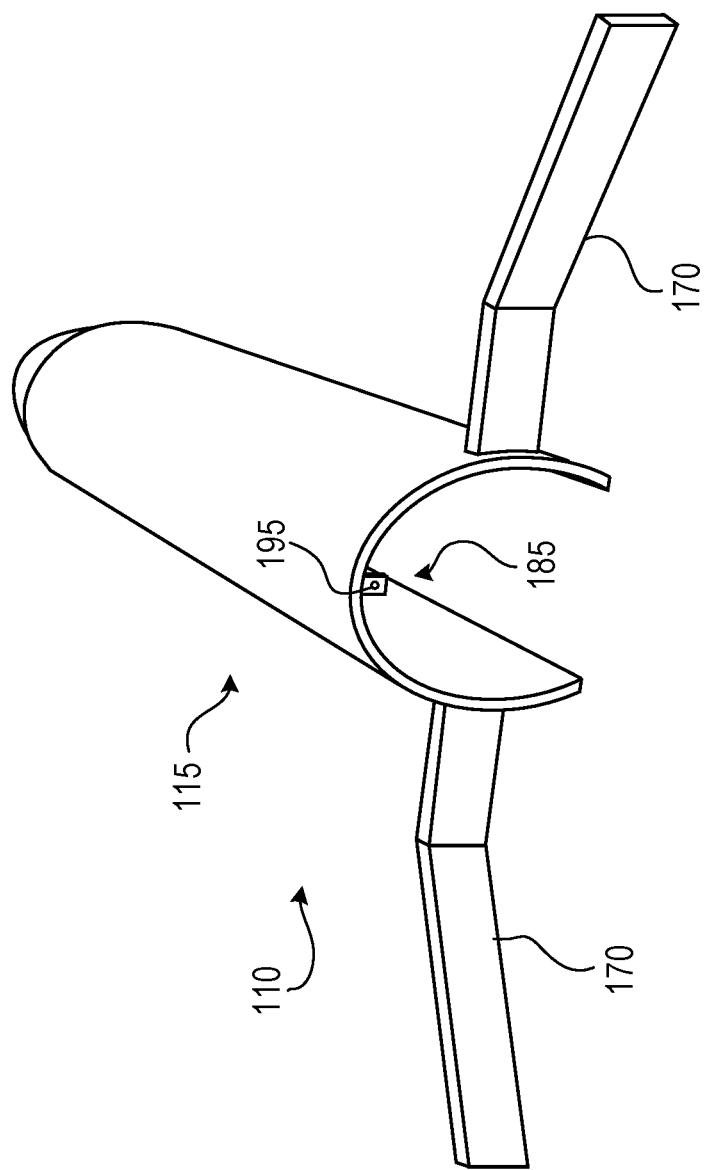
FIG. 4 depicts a back view of the proctoscope.

FIGS. 1, 2A-2B, and 3-4 depict an anal and rectal surgical diagnostic kit (100) which includes a first plurality of re-peelable double sided self-adhesive tapes (105) placed around an anal area of a patient and a proctoscope (110) inserted into an anus (see the circle between the plurality of re-peelable double sided self-adhesive tapes (105) as shown in FIG. 2A) of the patient. In a non-limiting embodiment, the first plurality of re-peelable double sided self-adhesive tapes (105) can have four re-peelable double sided self-adhesive tapes. In another non-limiting embodiment, the first plurality of re-peelable double sided self-adhesive tapes (105) can have a length of 5 cm and a width of 1.5 cm. The proctoscope (110) includes a longitudinal body (115) having a first portion (120), a second portion (125), and a third portion (130). In a non-limiting embodiment, the longitudinal body (115) can be U-shaped. In another non-limiting embodiment, the longitudinal body (115) can be transparent. The second portion (125) being located between the first portion (120) and the third portion (130). The third portion (130) being a converging portion (135) having a closed end (140). The first portion (120) being a non-converging portion (145) having an open end (150). Each of the first portion (120), the second portion (125), and the third portion (130) of the proctoscope (110) having a top surface (155), a plurality of middle surfaces (160), and a bottom surface (165). The top surfaces (155) and the plurality of middle surfaces (160) of each of the first portion (120), the second portion (125), and the third portion (130) are solid. The bottom surfaces (165) of at least the first portion (120) and the second portion (125) are hollow. The proctoscope (110) also includes a plurality of handles (170) attached to the longitudinal body (115). Each of the plurality of handles (170) are attached at an outer region (175) of each of the plurality of middle surfaces (160) of the first portion (120) of the proctoscope (110). In an embodiment, the plurality of handles (170) can have two handles (170). In certain embodiments, the plurality of handles (170) can have an angular surface. The proctoscope (110) additionally includes a second plurality of re-peelable double sided self-adhesive tapes (180) attached to the plurality of handles (170) to adhesively attach to the first plurality of re-peelable double sided self-adhesive tapes (105). Each of the second plurality of re-peelable double sided self-adhesive tapes (180) are attached to a side of each of the plurality of handles (170) facing in a direction toward the converging portion (135) of the third portion (130) of the proctoscope (110). In an embodiment, the second plurality of re-peelable double sided self-adhesive tapes (180) can have two re-peelable double sided self-adhesive tapes (180). In certain embodiments, each of the second plurality of re-peelable double sided self-adhesive tapes (180) cover an entire length of each of the plurality of handles (170). The proctoscope (110) further includes a cordless LED light (185) attached to an inner region (190) of the top surface (155) of the first portion (120) of the proctoscope (110) to light an internal area of the anus and the rectum of the patient. The cordless LED light (185) includes an on/off button (195).

The present subject matter also relates to a method of using the anal and rectal surgical diagnostic kit (100) for diagnosing and surgically removing gastrointestinal disorders in the anus and the rectum of the patient. The present method includes placing the first plurality of re-peelable double sided self-adhesive tapes (105) around the anal area of the patient; pressing the on/off button (195) on the cordless LED light (185) to turn the LED light on; inserting the converging portion (135) of the third portion (130) of the proctoscope (110) into the anus of the patient; aligning the plurality of handles (170) with the first plurality of re-peelable double sided self-adhesive tapes (105) as the proctoscope (110) is slowly pressed into the anus; and pushing the plurality of handles (170) against a buttock area of the patient while maintaining the alignment between the plurality of handles (170) and the first plurality of re-peelable double sided self-adhesive tapes (105) thereby adhesively attaching the second plurality of re-peelable double sided self-adhesive tapes (180) with the first plurality of re-peelable double sided self-adhesive tapes (105). In a non-limiting embodiment, multiple surgical tools (not shown) can be inserted into the longitudinal body (115) via the open end (150) of the first portion (120) of the proctoscope (110) to perform surgery on the anus and/or the rectum of the patient. Such surgery can include, but not limited to, surgically removing gastrointestinal disorders in the anus and the rectum such as hemorrhoids, polyps, and rectal or colon cancer. With the proctoscope (110) being adhesively secured to the anal area of the patient via the attachment between the first plurality of re-peelable double sided self-adhesive tapes (105) and the second plurality of re-peelable double sided self-adhesive tapes (180), the doctor can use both hands to operate the multiple surgical tools with ease and precision.

It is to be understood that the present processes, compositions, and methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An anal and rectal surgical diagnostic kit, comprising:
    a first plurality of re-peelable double sided self-adhesive tapes configured to be placed around an anal area surrounding an anus of a patient; and
    a proctoscope comprising:
    a longitudinal body having a first portion, a second portion, and a third portion, the second portion being located between the first portion and the third portion, the third portion being a converging portion having a closed end and the first portion being a non-converging portion having an open end, each of the first portion, the second portion, and the third portion of the proctoscope having a top surface, a plurality of middle surfaces, and a bottom surface, wherein the top surfaces and the plurality of middle surfaces of each of the first portion, the second portion, and the third portion are solid and the bottom surfaces of at least the first portion and the second portion are hollow;
    a plurality of handles attached to the longitudinal body, wherein each of the plurality of handles are attached at an outer region of each of the plurality of middle surfaces of the first portion of the proctoscope and wherein said plurality of handles are pushed against a buttock area of the patient such that said plurality of handles are configured to contact the first plurality of re-peelable double sided self-adhesive tapes configured to be placed around the anal area of the patient;
    a second plurality of re-peelable double sided self-adhesive tapes attached to the plurality of handles configured to adhesively attach to the first plurality of re-peelable double sided self-adhesive tapes, wherein each of the second plurality of re-peelable double sided self-adhesive tapes are attached to a side of each of the plurality of handles facing in a direction toward the converging portion of the third portion of the proctoscope and wherein the second plurality of re-peelable double sided self-adhesive tapes are attached to a plurality of handle segments, each handle segment proximal to an outer region of each of the plurality of middle surfaces of the first portion of the proctoscope; and
    a cordless LED light attached to an inner region of the top surface of the first portion of the proctoscope configured to light an internal area of an anus and a rectum of the patient, wherein the cordless LED light comprises an on/off button.

2. The anal and rectal surgical diagnostic kit of claim 1, wherein the first plurality of re-peelable double sided self-adhesive tapes comprises four re-peelable double sided self-adhesive tapes.

3. The anal and rectal surgical diagnostic kit of claim 1, wherein the longitudinal body is U-shaped.

4. The anal and rectal surgical diagnostic kit of claim 1, wherein the longitudinal body and the plurality of handles are transparent.

5. The anal and rectal surgical diagnostic kit of claim 1, wherein the plurality of handles comprises two handles.

6. The anal and rectal surgical diagnostic kit of claim 1, wherein each of the plurality of handles comprises an angular surface.

7. The anal and rectal surgical diagnostic kit of claim 1, wherein the second plurality of re-peelable double sided self-adhesive tapes comprises two re-peelable double sided self-adhesive tapes.

8. A method of using the anal and rectal surgical diagnostic kit of claim 1 for diagnosing and surgically removing gastrointestinal disorders in the anus and the rectum of the patient, the method comprising:
    placing the first plurality of re-peelable double sided self-adhesive tapes around the anal area of the patient;
    pressing the on/off button on the cordless LED light to turn the LED light on;
    inserting the converging portion of the third portion of the proctoscope into the anus of the patient;
    aligning the plurality of handles with the first plurality of re-peelable double sided self-adhesive tapes as the proctoscope is slowly pressed into the anus; and
    pushing the plurality of handles against a buttock area of the patient while maintaining the alignment between the plurality of handles and the first plurality of re-peelable double sided self-adhesive tapes thereby adhesively attaching the second plurality of re-peelable double sided self-adhesive tapes with the first plurality of re-peelable double sided self-adhesive tapes.

9. The method of using the anal and rectal surgical diagnostic kit for diagnosing and surgically removing gastrointestinal disorders in the anus and the rectum of a patient of claim 8, wherein the first plurality of re-peelable double sided self-adhesive tapes comprises four re-peelable double sided self-adhesive tapes.

10. The method of using the anus and rectal surgical diagnostic kit for diagnosing and surgically removing gastrointestinal disorders in the anal and the rectum of a patient of claim 8, wherein the longitudinal body is U-shaped.

11. The method of using the anus and rectal surgical diagnostic kit for diagnosing and surgically removing gastrointestinal disorders in the anal and the rectum of a patient of claim 8, wherein the longitudinal body and the plurality of handles are transparent.

12. The method of using the anal and rectal surgical diagnostic kit for diagnosing and surgically removing gastrointestinal disorders in the anus and the rectum of a patient of claim 8, wherein the plurality of handles comprises two handles.

13. The method of using the anal and rectal surgical diagnostic kit for diagnosing and surgically removing gastrointestinal disorders in the anus and the rectum of a patient of claim 8, wherein each of the plurality of handles comprises an angular surface.

14. The method of using the anal and rectal surgical diagnostic kit for diagnosing and surgically removing gastrointestinal disorders in the anus and the rectum of a patient of claim 8, wherein the second plurality of re-peelable double sided self-adhesive tapes comprises two re-peelable double sided self-adhesive tapes.

\* \* \* \* \*